US008376955B2

(12) United States Patent
Baker, Jr.

(10) Patent No.: US 8,376,955 B2
(45) Date of Patent: Feb. 19, 2013

(54) SPECTROSCOPIC METHOD AND SYSTEM FOR ASSESSING TISSUE TEMPERATURE

(75) Inventor: Clark R. Baker, Jr., Newman, CA (US)

(73) Assignee: Covidien LP, Mansfield, MA (US)

(*) Notice: Subject to any disclaimer, the term of this patent is extended or adjusted under 35 U.S.C. 154(b) by 588 days.

(21) Appl. No.: 12/569,721

(22) Filed: Sep. 29, 2009

(65) Prior Publication Data

US 2011/0077547 A1 Mar. 31, 2011

(51) Int. Cl.
*A61B 5/01* (2006.01)
*A61B 5/00* (2006.01)

(52) U.S. Cl. .................. 600/549; 600/310; 600/340

(58) Field of Classification Search .............. 600/310, 600/340, 549
See application file for complete search history.

(56) References Cited

U.S. PATENT DOCUMENTS

| | | |
|---|---|---|
| 3,638,640 A | 2/1972 | Shaw |
| 3,884,219 A | 5/1975 | Richardson et al. |
| 3,926,177 A | 12/1975 | Hardway et al. |
| 4,028,139 A | 6/1977 | Smith et al. |
| 4,714,341 A | 12/1987 | Hamaguri et al. |
| 4,805,623 A | 2/1989 | Jöbsis |
| 4,807,631 A | 2/1989 | Hersh et al. |
| 4,911,167 A | 3/1990 | Corenman et al. |
| 4,913,150 A | 4/1990 | Cheung et al. |
| 4,936,679 A | 6/1990 | Mersch |
| 4,938,218 A | 7/1990 | Goodman et al. |
| 4,971,062 A | 11/1990 | Hasebe et al. |
| 4,972,331 A | 11/1990 | Chance |
| 4,974,591 A | 12/1990 | Awazu et al. |
| 5,002,060 A | 3/1991 | Nedivi |
| 5,028,787 A | 7/1991 | Rosenthal et al. |
| 5,065,749 A | 11/1991 | Hasebe et al. |
| 5,084,327 A | 1/1992 | Stengel |
| 5,119,815 A | 6/1992 | Chance |
| 5,122,974 A | 6/1992 | Chance |
| 5,167,230 A | 12/1992 | Chance |
| 5,190,038 A | 3/1993 | Polson et al. |
| 5,246,003 A | 9/1993 | DeLonzor |
| 5,247,931 A | 9/1993 | Norwood |
| 5,263,244 A | 11/1993 | Centa et al. |
| 5,275,159 A | 1/1994 | Griebel |
| 5,279,295 A | 1/1994 | Martens et al. |
| 5,297,548 A | 3/1994 | Pologe |
| 5,355,880 A | 10/1994 | Thomas et al. |

(Continued)

FOREIGN PATENT DOCUMENTS

| | | |
|---|---|---|
| EP | 0615723 | 9/1994 |
| EP | 0630203 | 12/1994 |

(Continued)

OTHER PUBLICATIONS

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

(Continued)

*Primary Examiner* — Sean Dougherty

(57) ABSTRACT

According to various embodiments, a medical system and method for determining tissue temperature may include a spectroscopic sensor. The spectroscopic sensors may be configured to provide information about changes in water absorption profiles at one or more absorption peaks. Such sensors may be incorporated into ablation systems for tissue ablation. Temperature information may be used to determine the scope, volume, and/or depth of the ablation.

16 Claims, 5 Drawing Sheets

U.S. PATENT DOCUMENTS

| | | | |
|---|---|---|---|
| 5,372,136 A | 12/1994 | Steuer et al. | |
| 5,385,143 A | 1/1995 | Aoyagi | |
| 5,390,670 A | 2/1995 | Centa et al. | |
| 5,413,099 A | 5/1995 | Schmidt et al. | |
| 5,469,845 A | 11/1995 | DeLonzor et al. | |
| 5,482,036 A | 1/1996 | Diab et al. | |
| 5,483,646 A | 1/1996 | Uchikoga | |
| 5,553,614 A | 9/1996 | Chance | |
| 5,564,417 A | 10/1996 | Chance | |
| 5,575,285 A | 11/1996 | Takanashi et al. | |
| 5,611,337 A | 3/1997 | Bukta | |
| 5,630,413 A | 5/1997 | Thomas et al. | |
| 5,638,816 A | 6/1997 | Kiani-Azarbayjany et al. | |
| 5,645,059 A | 7/1997 | Fein et al. | |
| 5,645,060 A | 7/1997 | Yorkey | |
| 5,662,643 A * | 9/1997 | Kung et al. | 606/3 |
| 5,680,857 A | 10/1997 | Pelikan et al. | |
| 5,680,871 A | 10/1997 | Ganshorn | |
| 5,682,898 A | 11/1997 | Aung et al. | |
| 5,692,503 A | 12/1997 | Kuenstner | |
| 5,730,124 A | 3/1998 | Yamauchi | |
| 5,758,644 A | 6/1998 | Diab et al. | |
| 5,779,631 A | 7/1998 | Chance | |
| 5,782,757 A | 7/1998 | Diab et al. | |
| 5,786,592 A | 7/1998 | Hök | |
| 5,830,136 A | 11/1998 | DeLonzor et al. | |
| 5,830,139 A | 11/1998 | Abreu | |
| 5,831,598 A | 11/1998 | Kauffert et al. | |
| 5,842,981 A | 12/1998 | Larsen et al. | |
| 5,871,442 A | 2/1999 | Madarasz et al. | |
| 5,873,821 A | 2/1999 | Chance et al. | |
| 5,920,263 A | 7/1999 | Huttenhoff et al. | |
| 5,995,855 A | 11/1999 | Kiani et al. | |
| 5,995,856 A | 11/1999 | Mannheimer et al. | |
| 5,995,859 A | 11/1999 | Takahashi | |
| 6,011,986 A | 1/2000 | Diab et al. | |
| 6,064,898 A | 5/2000 | Aldrich | |
| 6,081,742 A | 6/2000 | Amano et al. | |
| 6,088,607 A | 7/2000 | Diab et al. | |
| 6,117,075 A | 9/2000 | Barnea | |
| 6,120,460 A | 9/2000 | Abreu | |
| 6,134,460 A | 10/2000 | Chance | |
| 6,150,951 A | 11/2000 | Olejniczak | |
| 6,154,667 A | 11/2000 | Miura et al. | |
| 6,163,715 A | 12/2000 | Larsen et al. | |
| 6,181,958 B1 | 1/2001 | Steuer et al. | |
| 6,181,959 B1 | 1/2001 | Schöllermann et al. | |
| 6,230,035 B1 | 5/2001 | Aoyagi et al. | |
| 6,266,546 B1 | 7/2001 | Steuer et al. | |
| 6,285,895 B1 | 9/2001 | Ristolainen et al. | |
| 6,309,352 B1 | 10/2001 | Oraevsky et al. | |
| 6,312,393 B1 | 11/2001 | Abreu | |
| 6,353,750 B1 | 3/2002 | Kimura et al. | |
| 6,397,091 B2 | 5/2002 | Diab et al. | |
| 6,405,069 B1 | 6/2002 | Oraevsky et al. | |
| 6,415,236 B2 | 7/2002 | Kobayashi et al. | |
| 6,419,671 B1 | 7/2002 | Lemberg | |
| 6,438,399 B1 | 8/2002 | Kurth | |
| 6,461,305 B1 | 10/2002 | Schnall | |
| 6,466,809 B1 | 10/2002 | Riley | |
| 6,487,428 B1 | 11/2002 | Culver et al. | |
| 6,487,439 B1 | 11/2002 | Skladnev et al. | |
| 6,501,974 B2 | 12/2002 | Huiku | |
| 6,501,975 B2 | 12/2002 | Diab et al. | |
| 6,514,278 B1 * | 2/2003 | Hibst et al. | 607/89 |
| 6,526,298 B1 * | 2/2003 | Khalil et al. | 600/310 |
| 6,526,301 B2 | 2/2003 | Larsen et al. | |
| 6,544,193 B2 | 4/2003 | Abreu | |
| 6,546,267 B1 | 4/2003 | Sugiura et al. | |
| 6,549,795 B1 | 4/2003 | Chance | |
| 6,580,086 B1 | 6/2003 | Schulz et al. | |
| 6,591,122 B2 * | 7/2003 | Schmitt | 600/310 |
| 6,594,513 B1 | 7/2003 | Jobsis et al. | |
| 6,606,509 B2 | 8/2003 | Schmitt | |
| 6,606,511 B1 | 8/2003 | Ali et al. | |
| 6,615,064 B1 | 9/2003 | Aldrich | |
| 6,618,042 B1 | 9/2003 | Powell | |
| 6,622,095 B2 | 9/2003 | Kobayashi et al. | |
| 6,654,621 B2 | 11/2003 | Palatnik et al. | |
| 6,654,624 B2 | 11/2003 | Diab et al. | |
| 6,658,276 B2 | 12/2003 | Kianl et al. | |
| 6,658,277 B2 | 12/2003 | Wasserman | |
| 6,662,030 B2 * | 12/2003 | Khalil et al. | 600/316 |
| 6,668,183 B2 | 12/2003 | Hicks et al. | |
| 6,671,526 B1 | 12/2003 | Aoyagi et al. | |
| 6,671,528 B2 | 12/2003 | Steuer et al. | |
| 6,678,543 B2 | 1/2004 | Diab et al. | |
| 6,679,837 B2 * | 1/2004 | Daikuzono | 600/157 |
| 6,684,090 B2 | 1/2004 | Ali et al. | |
| 6,690,958 B1 | 2/2004 | Walker et al. | |
| 6,697,658 B2 | 2/2004 | Al-Ali | |
| 6,708,048 B1 | 3/2004 | Chance | |
| 6,711,424 B1 | 3/2004 | Fine et al. | |
| 6,711,425 B1 | 3/2004 | Reuss | |
| 6,711,426 B2 | 3/2004 | Benaron et al. | |
| 6,714,245 B1 | 3/2004 | Ono | |
| 6,723,077 B2 | 4/2004 | Pickup et al. | |
| 6,731,274 B2 | 5/2004 | Powell | |
| 6,748,259 B1 | 6/2004 | Benaron et al. | |
| 6,785,568 B2 | 8/2004 | Chance | |
| 6,793,654 B2 | 9/2004 | Lemberg | |
| 6,801,797 B2 | 10/2004 | Mannheimer et al. | |
| 6,801,798 B2 | 10/2004 | Geddes et al. | |
| 6,801,799 B2 | 10/2004 | Mendelson | |
| 6,829,496 B2 | 12/2004 | Nagai et al. | |
| 6,850,053 B2 | 2/2005 | Daalmans et al. | |
| 6,855,112 B2 | 2/2005 | Kao et al. | |
| 6,863,652 B2 | 3/2005 | Huang et al. | |
| 6,873,865 B2 | 3/2005 | Steuer et al. | |
| 6,889,153 B2 | 5/2005 | Dietiker | |
| 6,898,451 B2 | 5/2005 | Wuori | |
| 6,939,307 B1 | 9/2005 | Dunlop | |
| 6,947,780 B2 | 9/2005 | Scharf | |
| 6,949,081 B1 | 9/2005 | Chance | |
| 6,957,094 B2 | 10/2005 | Chance et al. | |
| 6,961,598 B2 | 11/2005 | Diab | |
| 6,983,178 B2 | 1/2006 | Fine et al. | |
| 6,993,371 B2 | 1/2006 | Kiani et al. | |
| 6,996,427 B2 | 2/2006 | Ali et al. | |
| 7,024,235 B2 | 4/2006 | Melker et al. | |
| 7,027,849 B2 | 4/2006 | Al-Ali | |
| 7,030,749 B2 | 4/2006 | Al-Ali | |
| 7,035,697 B1 | 4/2006 | Brown | |
| 7,043,287 B1 * | 5/2006 | Khalil et al. | 600/310 |
| 7,047,056 B2 | 5/2006 | Hannula et al. | |
| 7,062,306 B2 | 6/2006 | Benaron et al. | |
| 7,083,593 B2 | 8/2006 | Stultz | |
| 7,127,278 B2 | 10/2006 | Melker et al. | |
| 7,162,306 B2 | 1/2007 | Caby et al. | |
| 7,184,148 B2 | 2/2007 | Alphonse | |
| 7,198,502 B2 | 4/2007 | Koenig et al. | |
| 7,209,775 B2 | 4/2007 | Bae et al. | |
| 7,236,811 B2 | 6/2007 | Schmitt | |
| 7,242,952 B2 | 7/2007 | Shirai et al. | |
| 7,254,425 B2 * | 8/2007 | Lowery et al. | 600/310 |
| 7,263,395 B2 | 8/2007 | Chan et al. | |
| 7,272,426 B2 | 9/2007 | Schmid | |
| 7,316,648 B2 | 1/2008 | Kelly et al. | |
| 7,327,463 B2 | 2/2008 | Alphonse | |
| 7,366,333 B2 | 4/2008 | Long et al. | |
| 7,373,193 B2 | 5/2008 | Al-Ali et al. | |
| 7,379,769 B2 | 5/2008 | Piron et al. | |
| 7,393,327 B2 | 7/2008 | Inukai et al. | |
| 7,400,257 B2 | 7/2008 | Rivas | |
| 7,447,388 B2 | 11/2008 | Bates et al. | |
| 7,734,321 B2 * | 6/2010 | White | 600/310 |
| 2001/0005773 A1 | 6/2001 | Larsen et al. | |
| 2001/0020122 A1 | 9/2001 | Steuer et al. | |
| 2001/0039376 A1 | 11/2001 | Steuer et al. | |
| 2001/0044700 A1 | 11/2001 | Kobayashi et al. | |
| 2002/0026106 A1 | 2/2002 | Khalil et al. | |
| 2002/0035318 A1 | 3/2002 | Mannheimer et al. | |
| 2002/0038079 A1 | 3/2002 | Steuer et al. | |
| 2002/0042558 A1 | 4/2002 | Mendelson | |
| 2002/0049389 A1 | 4/2002 | Abreu | |
| 2002/0062071 A1 | 5/2002 | Diab et al. | |
| 2002/0111748 A1 | 8/2002 | Kobayashi et al. | |

| | | | |
|---|---|---|---|
| 2002/0133068 A1 | 9/2002 | Huiku | |
| 2002/0156354 A1 | 10/2002 | Larson | |
| 2002/0161287 A1 | 10/2002 | Schmitt | |
| 2002/0161290 A1 | 10/2002 | Chance | |
| 2002/0165439 A1 | 11/2002 | Schmitt | |
| 2002/0183727 A1* | 12/2002 | Daikuzono | 606/10 |
| 2002/0198443 A1 | 12/2002 | Ting | |
| 2003/0023140 A1 | 1/2003 | Chance | |
| 2003/0055324 A1 | 3/2003 | Wasserman | |
| 2003/0060693 A1 | 3/2003 | Monfre et al. | |
| 2003/0084907 A1* | 5/2003 | Pacek et al. | 128/898 |
| 2003/0139687 A1 | 7/2003 | Abreu | |
| 2003/0144584 A1 | 7/2003 | Mendelson | |
| 2003/0203357 A1* | 10/2003 | Huang | 435/5 |
| 2003/0220548 A1 | 11/2003 | Schmitt | |
| 2003/0220576 A1 | 11/2003 | Diab | |
| 2004/0010188 A1 | 1/2004 | Wasserman | |
| 2004/0054270 A1 | 3/2004 | Pewzner et al. | |
| 2004/0087846 A1 | 5/2004 | Wasserman | |
| 2004/0087916 A1 | 5/2004 | Pickup et al. | |
| 2004/0107065 A1 | 6/2004 | Al-Ali | |
| 2004/0127779 A1 | 7/2004 | Steuer et al. | |
| 2004/0171920 A1 | 9/2004 | Mannheimer et al. | |
| 2004/0176670 A1 | 9/2004 | Takamura et al. | |
| 2004/0176671 A1 | 9/2004 | Fine et al. | |
| 2004/0181196 A1 | 9/2004 | Pickup et al. | |
| 2004/0230106 A1 | 11/2004 | Schmitt et al. | |
| 2005/0054907 A1 | 3/2005 | Page et al. | |
| 2005/0080323 A1 | 4/2005 | Kato | |
| 2005/0101850 A1 | 5/2005 | Parker | |
| 2005/0113651 A1 | 5/2005 | Wood et al. | |
| 2005/0113656 A1 | 5/2005 | Chance | |
| 2005/0154285 A1 | 7/2005 | Neason | |
| 2005/0154286 A1 | 7/2005 | Neason | |
| 2005/0165316 A1* | 7/2005 | Lowery et al. | 600/480 |
| 2005/0165323 A1 | 7/2005 | Montgomery et al. | |
| 2005/0168722 A1 | 8/2005 | Forstner et al. | |
| 2005/0177034 A1 | 8/2005 | Beaumont | |
| 2005/0192488 A1 | 9/2005 | Bryenton et al. | |
| 2005/0201345 A1 | 9/2005 | Williamson | |
| 2005/0203357 A1 | 9/2005 | Debreczeny et al. | |
| 2005/0228248 A1 | 10/2005 | Dietiker | |
| 2005/0267346 A1 | 12/2005 | Faber et al. | |
| 2005/0283059 A1 | 12/2005 | Iyer et al. | |
| 2006/0004270 A1* | 1/2006 | Bedard et al. | 600/316 |
| 2006/0009688 A1 | 1/2006 | Lamego et al. | |
| 2006/0015021 A1 | 1/2006 | Cheng | |
| 2006/0020181 A1 | 1/2006 | Schmitt | |
| 2006/0020309 A1* | 1/2006 | Altshuler et al. | 607/88 |
| 2006/0030763 A1 | 2/2006 | Mannheimer et al. | |
| 2006/0052680 A1 | 3/2006 | Diab | |
| 2006/0058683 A1 | 3/2006 | Chance | |
| 2006/0064024 A1 | 3/2006 | Schnall | |
| 2006/0111622 A1* | 5/2006 | Merritt et al. | 600/315 |
| 2006/0122475 A1 | 6/2006 | Balberg et al. | |
| 2006/0129204 A1 | 6/2006 | Pless | |
| 2006/0142808 A1 | 6/2006 | Pearce et al. | |
| 2006/0167367 A1 | 7/2006 | Stanczak et al. | |
| 2006/0178588 A1 | 8/2006 | Brody | |
| 2006/0195028 A1 | 8/2006 | Hannula et al. | |
| 2006/0206018 A1* | 9/2006 | Abul-Haj et al. | 600/316 |
| 2006/0217602 A1* | 9/2006 | Abul-Haj et al. | 600/316 |
| 2006/0224058 A1 | 10/2006 | Mannheimer | |
| 2006/0229515 A1* | 10/2006 | Sharareh et al. | 600/476 |
| 2006/0247501 A1 | 11/2006 | Ali | |
| 2006/0247506 A1 | 11/2006 | Balberg et al. | |
| 2006/0258921 A1 | 11/2006 | Addison et al. | |
| 2006/0265022 A1 | 11/2006 | John et al. | |
| 2006/0272418 A1 | 12/2006 | Maris et al. | |
| 2006/0272419 A1 | 12/2006 | Maris et al. | |
| 2007/0118045 A1 | 5/2007 | Naghavi et al. | |
| 2008/0060138 A1 | 3/2008 | Price et al. | |
| 2008/0096495 A1 | 4/2008 | Shen | |
| 2008/0208912 A1 | 8/2008 | Garibaldi | |
| 2008/0214903 A1 | 9/2008 | Orbach | |
| 2008/0221409 A1* | 9/2008 | Hoarau | 600/310 |
| 2008/0312533 A1 | 12/2008 | Balberg et al. | |
| 2010/0049180 A1* | 2/2010 | Wells et al. | 606/12 |
| 2011/0108730 A1* | 5/2011 | Herrmann | 250/339.04 |

FOREIGN PATENT DOCUMENTS

| | | |
|---|---|---|
| EP | 1491135 | 12/2004 |
| EP | 1986543 | 11/2008 |
| JP | 63275325 | 11/1988 |
| JP | 3170866 | 7/1991 |
| JP | 3238813 | 10/1991 |
| JP | 4332536 | 11/1992 |
| JP | 7124138 | 5/1995 |
| JP | 7136150 | 5/1995 |
| JP | 2004008572 | 1/2004 |
| JP | 2004113353 | 4/2004 |
| JP | 2004194908 | 7/2004 |
| JP | 2004248819 | 9/2004 |
| JP | 2004290545 | 10/2004 |
| JP | 2005034472 | 2/2005 |
| WO | WO9101678 | 2/1991 |
| WO | WO9309711 | 5/1993 |
| WO | WO9639927 | 12/1996 |
| WO | WO9843071 | 10/1998 |
| WO | WO9932030 | 7/1999 |
| WO | WO0021438 | 4/2000 |
| WO | WO0140776 | 6/2001 |
| WO | WO0176461 | 10/2001 |
| WO | WO0176471 | 10/2001 |
| WO | WO03039326 | 5/2003 |
| WO | WO2005025399 | 3/2005 |
| WO | WO2006097910 | 9/2006 |

OTHER PUBLICATIONS

Nijland, Roel, et al.; "Validation of Reflectance Pulse Oximetry: An Evaluation of a new Sensor in Piglets," *Journal of Clinical Monitoring*, vol. 13, pp. 43-49 (1997).

Nogawa, Masamichi, et al.; "A New Hybrid Reflectance Optical Pulse Oximetry Sensor for Lower Oxygen Saturation Measurement and for Broader Clinical Application," *SPIE*, vol. 2976, pp. 78-87 (1997).

Mannheimer, Paul D., et al.; "Wavelength Selection for Low-Saturation Pulse Oximetry," *IEEE Transactions on Biomedical Engineering*, vol. 44, No. 3, pp. 148-158 (Mar. 1997).

Pickett, John, et al.; "Pulse Oximetry and PPG Measurements in Plastic Surgery," *Proceedings—19th International Conference—IEEE/EMBS*, Chicago, Illinois, Oct. 30-Nov. 2, 1997, pp. 2330-2332.

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

East, Christine E., et al.; "Fetal Oxygen Saturation and Uterine Contractions During Labor," *American Journal of Perinatology*, vol. 15, No. 6, pp. 345-349 (Jun. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engineering in Medicine and Biology Society*, vol. 20, No. 6, 1998.

Such, Hans Olaf; "Optoelectronic Non-invasive Vascular Diagnostics Using multiple Wavelength and Imaging Approach," *Dissertation*, (1998).

Lutter, N., et al.; "Comparison of Different Evaluation Methods for a Multi-wavelength Pulse Oximeter," *Biomedizinische Technik*, vol. 43, (1998).

Todd, Bryan, et al.; "The Identification of Peaks in Physiological Signals," *Computers and Biomedical Research*, vol. 32, pp. 322-335 (1999).

Seelbach-Göbel, Birgit, et al.; "The prediction of fetal acidosis by means of intrapartum fetal pulse oximetry," *Am J. Obstet. Gynecol.*, vol. 180, No. 1, Part 1, pp. 73-81 (1999).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Kaestle, S.; "Determining Artefact Sensitivity of New Pulse Oximeters in Laboratory Using Signals Obtained from Patient," *Biomedizinische Technik*, vol. 45 (2000).

Cysewska-Sobusaik, Anna; "Metrological Problems With noninvasive Transillumination of Living Tissues," *Proceedings of SPIE*, vol. 4515, pp. 15-24 (2001).

Belal, Suliman Yousef, et al.; "A fuzzy system for detecting distorted plethysmogram pulses in neonates and paediatric patients," *Physiol. Meas.*, vol. 22, pp. 397-412 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Chan, K.W., et al.; "17.3: Adaptive Reduction of Motion Artifact from Photoplethysmographic Recordings using a Variable Step-Size LMS Filter," *IEEE*, pp. 1343-1346 (2002).

Yoon, Gilwon, et al.; "Multiple diagnosis based on Photoplethysmography: hematocrit, SpO2, pulse and respiration," *Optics in Health Care and Biomedical optics: Diagnostics and Treatment; Proceedings of the SPIE*, vol. 4916; pp. 185-188 (2002).

Lopez-Silva, Sonnia Maria Lopez, et al.; "Near-infrared transmittance pulse oximetry with laser diodes," *Journal of Biomedical Optics*, vol. 8, No. 3, pp. 525-533 (Jul. 2003).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Johansson, A.; "Neural network for photoplethysmographic respiratory rate monitoring," *Medical & Biological Engineering & Computing*, vol. 41, pp. 242-248 (2003).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Crespi, F., et al.; "Near infrared oxymeter prototype for non-invasive analysis of rat brain oxygenation," *Optical Sensing, Proceedings of SPIE*, vol. 5459, pp. 38-45 (2004).

Johnston, W.S., et al.; "Extracting Breathing Rate Infromation from a Wearable Reflectance Pulse Oximeter Sensor," *Proceedings of the 26th Annual International conference of the IEEE EMBS*, San Francisco, California; Sep. 1-5, 2004; pp. 5388-5391.

Spigulis, Janis, et al.; "Optical multi-channel sensing of skin blood pulsations," *Optical Sensing, Proceedings of SPIE*, vol. 5459, pp. 46-53 (2004).

* cited by examiner

SPECTROSCOPIC METHOD AND SYSTEM FOR ASSESSING TISSUE TEMPERATURE

BACKGROUND

The present disclosure relates generally to medical devices and, more particularly, to the use of spectroscopy to monitor changes in the temperature of water-bearing tissue.

This section is intended to introduce the reader to aspects of the art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Some forms of patient treatment involve removing unwanted portions of tissue from the patient, for example by surgical resection. However, for tissue areas that may be difficult to access surgically or for very small areas of tissue, tissue ablation may be more appropriate. Tissue ablation uses energy directed at the tissue site of interest to heat the tissue to temperatures that destroy the viability of the individual components of the tissue cells. During tissue ablation, an unwanted portion of a tissue, e.g., fibrous tissue, lesions, or obstructions, may be destroyed. Ablation can be achieved by various techniques, including the application of radio frequency energy, microwave energy, lasers, and ultrasound. Generally, ablation procedures involve ablating tissue that is surrounded by otherwise healthy tissue that a clinician wishes to preserve. Accordingly, better therapeutic outcomes may be achieved through precise application of the ablating energy to the tissue.

The precision of the ablation may depend in part on the type of energy applied, the skill of the clinician, and the accessibility of the tissue in question. For example, ablation may be complex if the target area is moving. During catheter ablation to correct an abnormal heartbeat, the cardiac tissue in question is typically in motion, which may affect the volume of tissue ablated. Because the ablation may take place internally, as in the case of cardiac ablation, assessment of the volume of the tissue necrosis may be difficult. In addition, depending on the type of ablating energy used, controlling the area of the ablation may be easier than controlling the depth of the ablation. Accordingly, the depth of the necrosis may vary from patient to patient.

BRIEF DESCRIPTION OF THE DRAWINGS

Advantages of the disclosure may become apparent upon reading the following detailed description and upon reference to the drawings in which.

DETAILED DESCRIPTION

Figure 1:
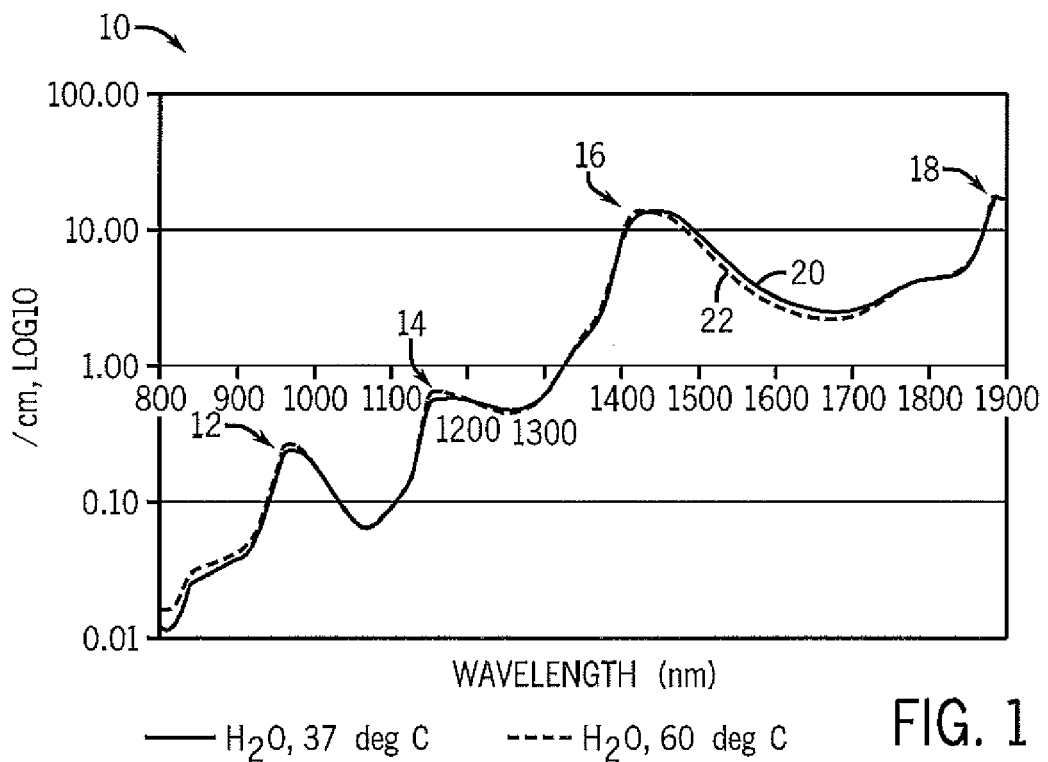
FIG. 1 is a graph of the absorption spectra for water for two different temperature points.

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Provided herein are systems, sensors, and methods for spectroscopic monitoring of tissue temperature. When such systems are used in conjunction with a tissue ablation device, a medical monitor may assess changes in spectrophotometric parameters to determine the viability of a probed area of the tissue. Tissue areas with water absorption profiles characteristic of particular temperatures may be determined. Such systems may also be used to determine the viability of the probed tissue, i.e., probed tissues associated with temperatures above a certain threshold may be considered nonviable. As a result, the efficacy of the ablation may be determined. In other embodiments, the spectroscopic sensors as provided may be used in conjunction with other types of medical procedures that involve changing or monitoring tissue temperature, such as hypothermic or hyperthermic treatments.

Monitoring the necrosis of ablated tissue may be complex, particularly when using techniques that involve ablation of internal tissue. As provided herein, spectroscopic sensing may be used to noninvasively monitor tissue temperature at a number of tissue depths. The temperature information may then be used to determine the scope of the tissue ablation. Generally, ablated tissue cells will have characteristically higher temperatures as a result of the heat of ablation. During ablation, the tissue is heated until the resultant higher temperature of the tissue causes protein denaturation and other effects that lead to necrosis of the tissue. The temperature changes may be monitored by spectroscopically assessing changes in the shape, position and/or magnitude of one or more water absorption peaks of the tissue. Because wavelengths may be chosen that penetrate known depths of the patient's tissue, temperature information may be collected for relatively fine gradations of tissue depth that are otherwise difficult to obtain. Such noninvasive monitoring may provide information about the depth and/or volume of the tissue ablation and may allow clinicians to more precisely determine whether further ablating treatment may be needed. In addition, clinicians may be able to determine the borders of any ablated tissue in relation to the healthy tissue and may be able to match the borders with previously acquired data (e.g., cardiac images or tumors) to determine if the scope of the ablated tissue corresponds with the size, location and/or shape of, for example, known obstructions or tumors.

Sensors as provided may be applied to a patient's skin and/or internal organs (e.g., as part of a catheter or other inserted assembly) to monitor multiple absorption peaks of water, for example in the red or near infrared spectrum. While other potential absorbers may make up some percentage of the content of a patient's tissue, many of these absorbers, such as lipid and hemoglobin, do not change their absorption profiles significantly with temperature. For this reason, the absorption of water or other constituents whose absorption, as measured spectroscopically, changes with temperature may provide more information that relates to the tissue temperature. Accordingly, by monitoring changes in the water absorption profile that occur with rising temperatures for a single area of tissue (e.g., pre and post-ablation), a change in temperature for the tissue area may be estimated. To account for the variation in light scattering, a change may be measured against a pre-ablation spectrum. In addition, such information may be combined with a measured patient baseline temperature, either local or systemic, to determine the extent of tissue temperature changes. The near-infrared peaks of water shift and narrow with increasing temperature due to increases in hydrogen bonding between water molecules. FIG. 1 is a graph 10 of successive absorption peaks 12, 14, 16, and 18 (corresponding to peaks centered near approximately 975, 1180, 1450, and 1900, respectively). Shown are the shape and position of the absorption peaks for water at 37° C., shown by data 20, and at 60° C., shown by data 22, plotted against the depth of tissue penetration. As illustrated, the water at 60° C. is shown to have a different characteristic absorption profile.

Figure 2:
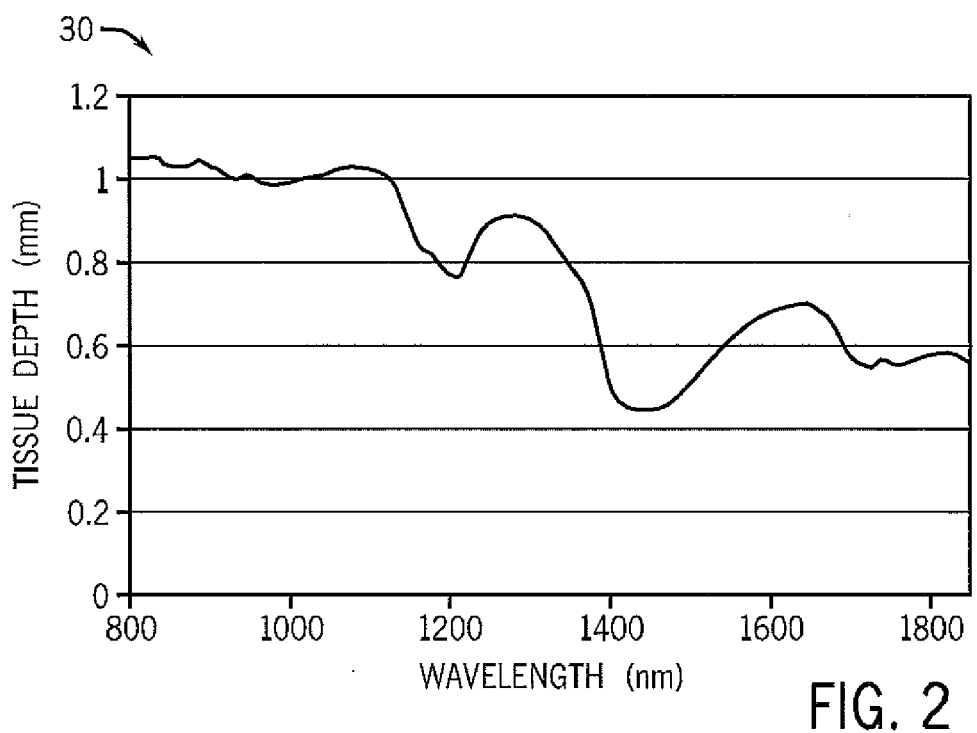
FIG. 2 is a graph of estimated mean photon penetration depth plotted against wavelength for a sample of 70% lean water concentration and an emitter-detector spacing of 2.5 mm.

FIG. 2 is a graph 30 of estimated photon penetration depth into tissue plotted against wavelength for light emitted into tissue and detected by a detector spaced approximately 2.5 mm from the emitter. In the depicted simulation, the tissue sample is assumed to have 70% lean water concentration, which is approximately the lean water concentration of typical tissue. As shown, over a portion of the spectrum, the penetration depth varies with wavelength. Accordingly, a particular wavelength is associated with a particular penetration depth for a particular emitter-detector spacing. By using a sensor or a combination of sensors with different emitter-detector spacings as well as different wavelengths, multiple spectroscopic temperature estimates corresponding to multiple tissue depths may be combined to estimate a thermal gradient that is predictive of the total volume of tissue that has been rendered nonviable by ablation.

Figure 3:
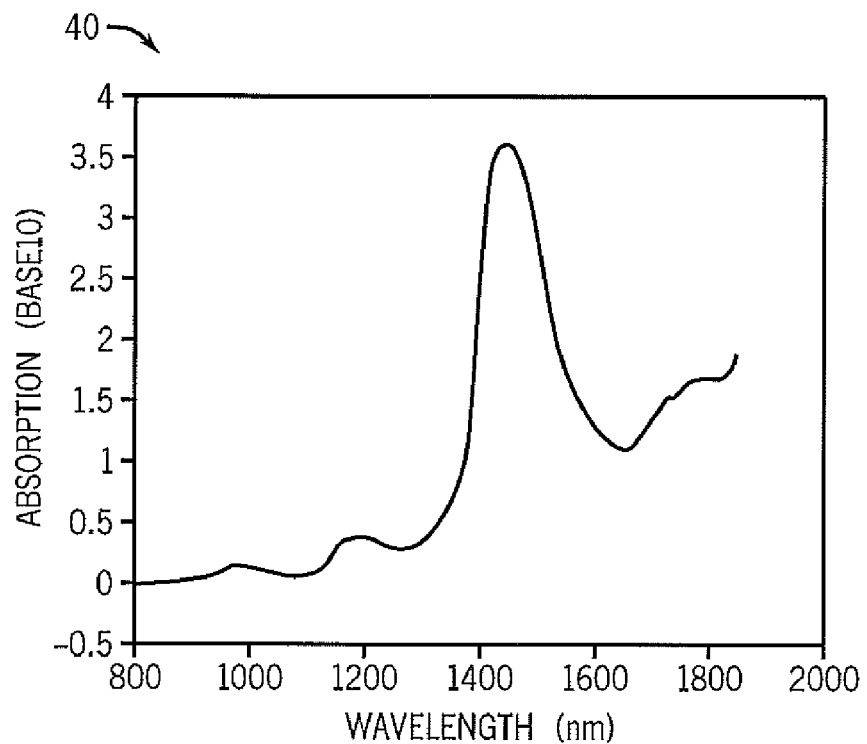
FIG. 3 is a graph of a simulated absorption spectrum of water for an example tissue sample at 37° C. and an emitter-detector spacing of 2.5 mm.
Figure 4:
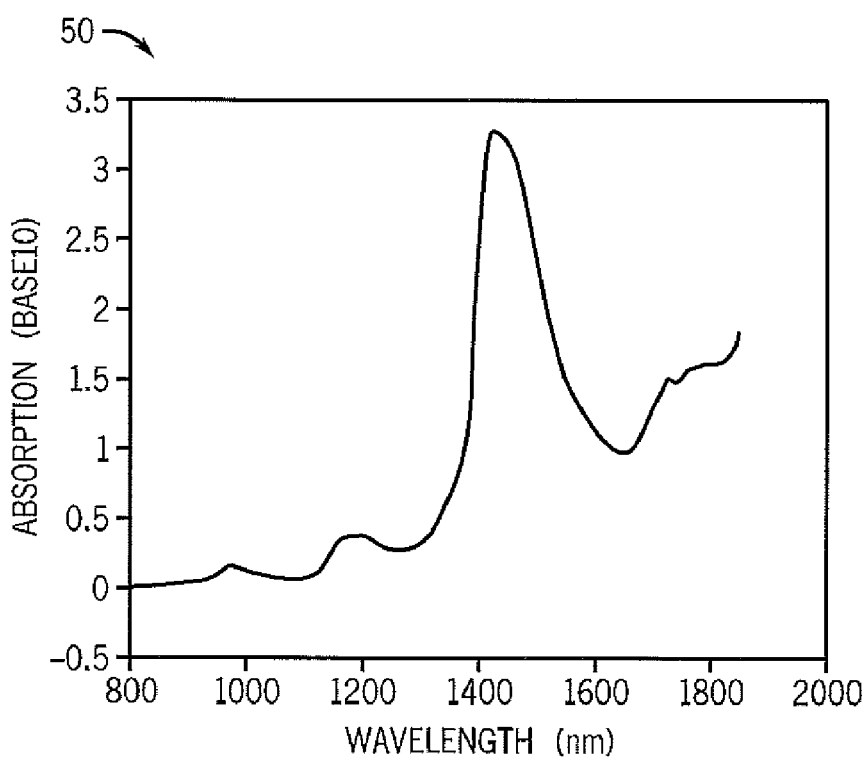
FIG. 4 is a graph of a simulated absorption spectrum of water for an example tissue sample at 50-60° C. and an emitter-detector spacing of 2.5 mm.
Figure 5:
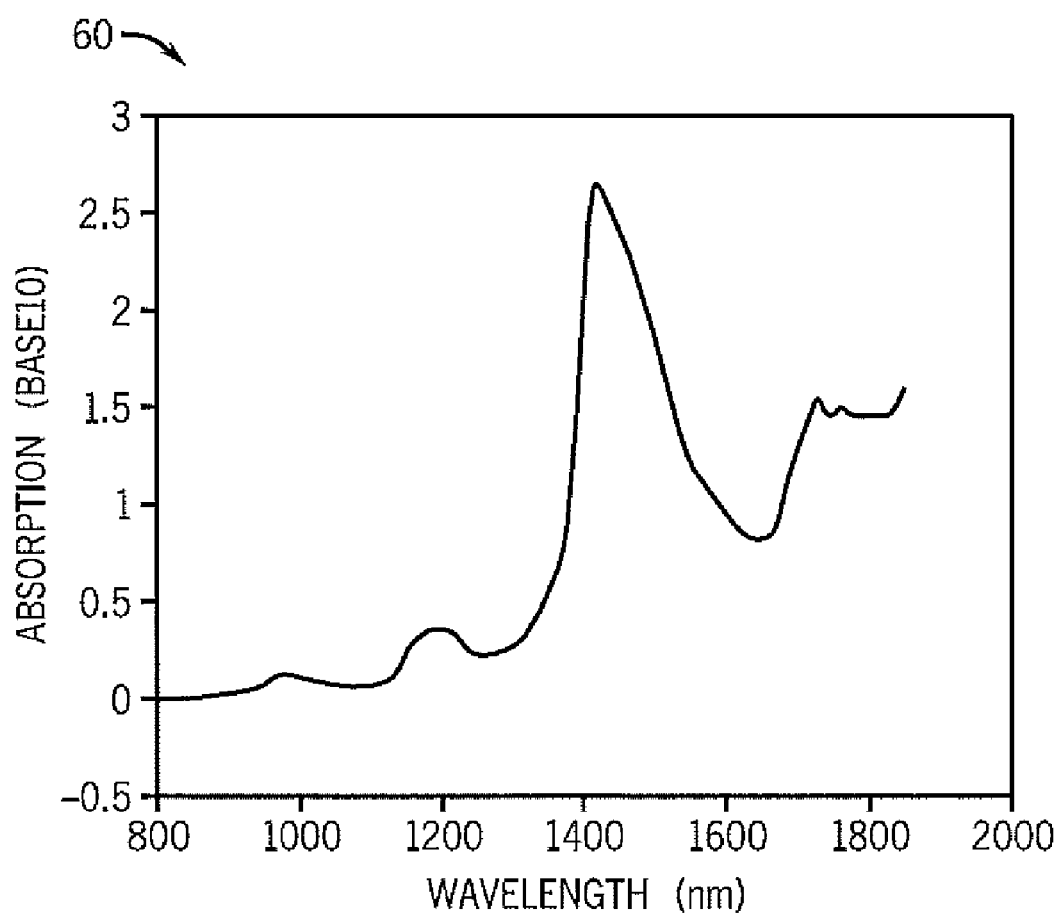
FIG. 5 is a graph of a simulated absorption spectrum of water for an example tissue sample at 60-80° C. and an emitter-detector spacing of 2.5 mm.

Simulations of the types of shifts seen at different tissue temperatures are depicted in FIGS. 3-5, with all simulations assuming a 2.5 mm separation between emitter and detector, with both facing the same direction and embedded in tissue at or near the heating source. For each exemplary simulated tissue spectrum, multi-linear regressions were performed against experimentally determined tissue component spectra of water, protein, and lipid, plus the derivative of water absorption with respect to temperature. These regressions were performed using data over the spectral ranges of 945-1035 nm, 1127-1170 nm, and 1360-1570 nm, corresponding to regions of tissue spectrum where water is the dominant absorber and where water absorption changes significantly with temperature. Mean photon penetration depths were determined to be, respectively, 0.94 mm, 0.86 mm, and 0.52 mm for these spectral ranges, and did not differ significantly between these examples. However, in certain embodiments, depending ion the nature and temperature of ablation, a significant decrease in tissue water content may occur after ablation. A decrease in water content may allow deeper penetration for a particular wavelength. Accordingly, the mean photon penetration may increase over the course of the ablation. Such effects may be accounted for in determining the temperature gradient for a particular tissue sample. Similar temperature estimates may be obtained via other methods of comparing tissue spectra to features of tissue component spectra. For example, regressions may be performed between derivatives, or other mathematical functions, of tissue and component spectra.

Table I below shows the resulting temperatures estimated from the multi-linear regressions corresponding to each example and spectral range. As shown, the temperatures increase over the course of the ablation.

| Spectral Range | Temp FIG. 1 | Temp FIG. 2 | Temp FIG. 3 |
| --- | --- | --- | --- |
| 945-1035 nm | 36.83° C. | 49.45° C. | 58.45° C. |
| 1127-1170 nm | 37.55° C. | 47.33° C. | 60.43° C. |
| 1360-1570 nm | 37.52° C. | 60.64° C. | 82.16° C. |

The example shown in FIG. 3 is a graph 40 of absorption at multiple mean photon penetration depths at a plurality of near infrared water absorption peaks. The mean photon penetration depths may be estimated by using a graph similar to FIG. 2 of mean photon distribution for a particular emitter-detector spacing. Prior to heating, tissue is simulated at 37° C., assuming a tissue composition of 66% water, 24% protein, and 10% lipid. Because this corresponds to a pre-ablation tissue temperature, the temperature at different depths is generally about 37° C., corresponding to normal body temperature, before any heating through ablation occurs.

After ablation begins, the temperature of the tissue starts to rise and the water absorption profile begins to show characteristic shifting. FIG. 4 is a graph 50 of a simulation of tissue heating during the course of ablation. At a depth of 0.5 mm, the temperature was simulated to be 60° C., changing linearly to 50° C. at a distance of 1.0 mm. This corresponds with the temperature being highest closer to the ablating source and lower the farther away from the source. The tissue is assumed to have dried out during heating to a composition of 58% water, 30% protein, and 12% lipid. As shown, the center of the water absorption peak in the 1350-1600 nm range has shifted toward the shorter wavelengths as a result of temperature change.

After the ablation is completed, the temperatures have reached their highest point in the tissue and the affected region is rendered nonviable. FIG. 5 is a graph 60 of temperatures reached shortly after the completion of an ablating course of energy. At a depth of 0.5 mm, the temperature was simulated to be 80° C., changing linearly to 60° C. at a distance of 1.0 mm. The tissue is assumed to have dried out further due to continued heating, to a composition of 40% water, 42% protein, and 17% lipid. As shown, the center of the water absorption peak in the 1350-1600 nm range has shifted toward the shorter wavelengths as a result of temperature change. A shifting and narrowing of the water absorption peak in the 1350-1600 nm range may be observed.

Figure 6:
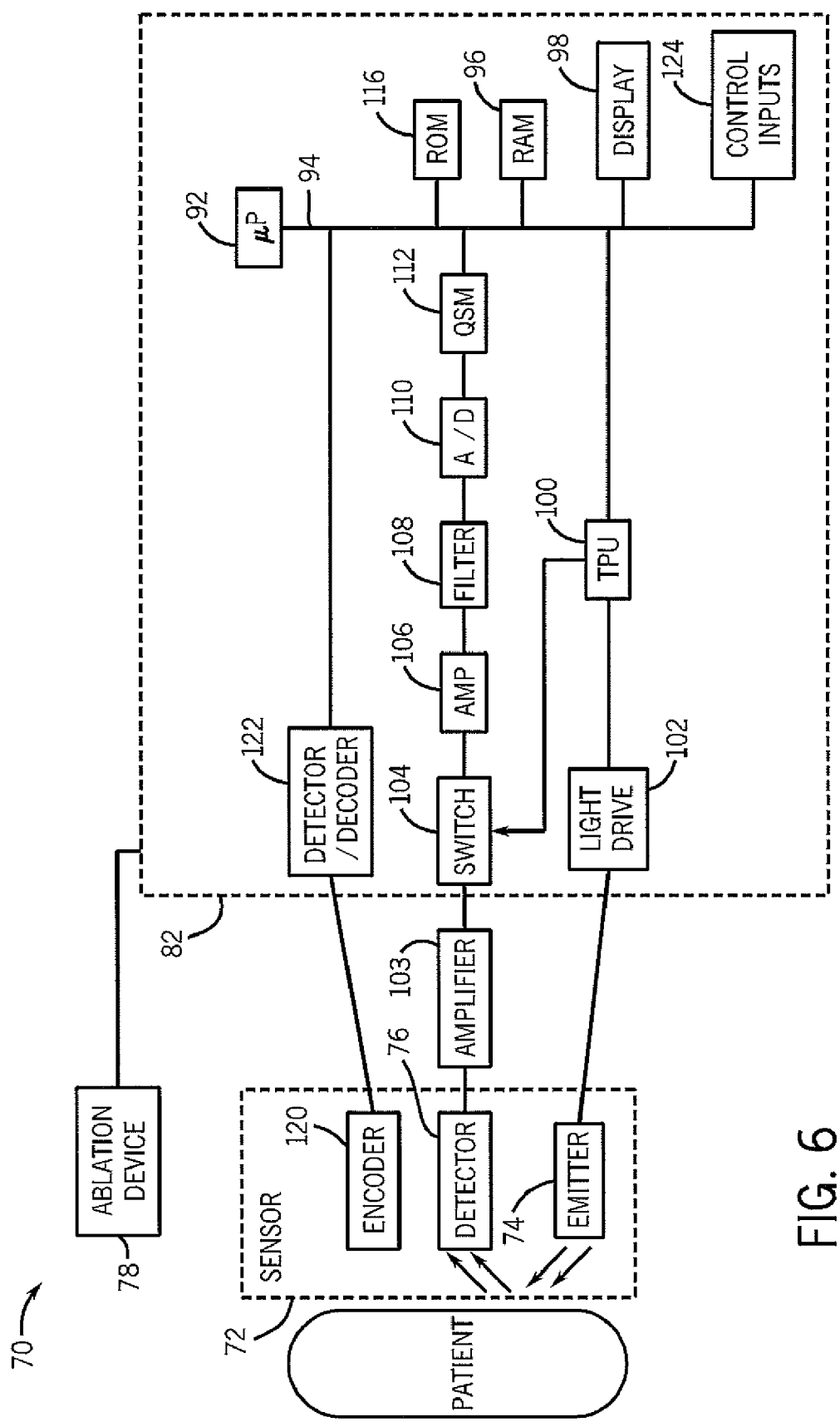
FIG. 6 is a block diagram of a system for monitoring tissue temperature according to an embodiment.

FIG. 6 shows a system 70 that may be used for monitoring temperature in conjunction with an ablation procedure. The system 70 includes a spectroscopic sensor 72 with a light emitter 74 and detector 76 that may be of any suitable type. The emitter 74 may be a broad spectrum emitter or may be configured to emit light of a limited wavelength range or at select discrete wavelengths. In one embodiment, the emitter 72 may include a filter wheel for tuning a broad spectrum to a series of particular wavelengths. The emitter 74 may be one or more light emitting diodes adapted to transmit one or more wavelengths of light in the red to infrared range, and the detector 76 may be a photodetector configured to receive the emitted light. In specific embodiments, the emitter 74 may be a laser diode or a vertical cavity surface emitting laser (VCSEL). The laser diode may be a tunable laser, such that a single diode may be tuned to various wavelengths corresponding to a number of absorption peaks of water. Depending on the particular arrangement of the sensor 72, the emitter 74 may be associated with an optical fiber for transmitting the emitted light into the tissue. The light may be any suitable wavelength corresponding to the wavelengths absorbed by water. For example, wavelengths between about 800 nm, corresponding with far-red visible light, and about 1800 nm, in the near infrared range, may be absorbed by water.

By way of example, FIG. 6 shows an ablation device 78 that may be associated with the system 70. However, it should be understood that ablation device 78 is merely illustrative of a medical device that may be used in conjunction with a spectroscopic sensor 72 for monitoring temperature and other devices may be incorporated into the system 70 if appropriate. In certain embodiments, the ablation device may be a microwave ablation device 78. In one embodiment, the sensor 72 is structurally associated (e.g., is disposed on) the ablation device, for example the emitter 74 and the detector 76 are disposed on a catheter, such as a cardiac catheter, or other implantable portion of the device. In embodiments in which the ablation takes place on the surface of the skin, the emitter and detector may be part of a housing or other support structure for the ablation energy source.

An associated monitor 82 may receive signals, for example from the spectroscopy sensor 72 through a sensor interface (e.g., a sensor port or a wireless interface) and, in embodiments, from the ablation device 78, to determine if the ablation has generated sufficiently high tissue temperature to destroy the viability of the tissue in the area of interest. The monitor 82 may include appropriate processing circuitry for determining temperature parameters, such as a microprocessor 92, which may be coupled to an internal bus 94. Also connected to the bus may be a RAM memory 96 and a display 98. A time processing unit (TPU) 100 may provide timing control signals to light drive circuitry 102, which controls when the emitter 74 is activated, and, if multiple light sources are used, the multiplexed timing for the different light sources, TPU 100 may also control the gating-in of signals from the sensor 72 and amplifier 103 and a switching circuit 104. These signals are sampled at the proper time, depending at least in part upon which of multiple light sources is activated, if multiple light sources are used. The received signal from the sensor 72 may be passed through an amplifier 106, a low pass filter 108, and an analog-to-digital converter 110. The digital data may then be stored in a queued serial module (QSM) 112, for later downloading to RAM 96 as QSM 112 fills up.

In an embodiment, based at least in part upon the received signals corresponding to the water absorption peaks received by detector 76 of the sensor 72, microprocessor 92 may calculate the microcirculation parameters using various algorithms. In addition, the microprocessor 92 may calculate tissue temperature. These algorithms may employ certain coefficients, which may be empirically determined, and may correspond to the wavelength of light used. In addition, the algorithms may employ additional correction coefficients. The algorithms and coefficients may be stored in a ROM 116 or other suitable computer-readable storage medium and accessed and operated according to microprocessor 92 instructions. In one embodiment, the correction coefficients may be provided as a lookup table. In addition, the sensor 72 may include certain data storage elements, such as an encoder 120, that may encode information related to the characteristics of the sensor 72, including information about the emitter 74 and the detector 76. The information may be accessed by detector/decoder 122, located on the monitor 82. Control inputs 124 may allow an operator to input patient and/or sensor characteristics.

Figure 7:
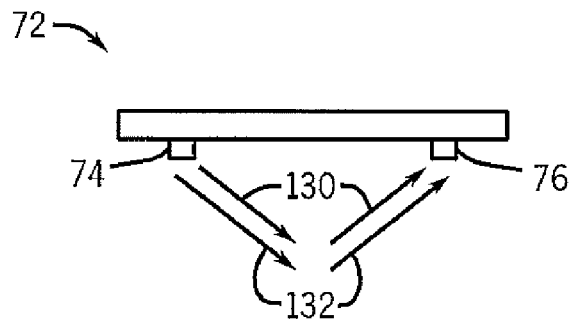
FIG. 7 is a side view of an example of a spectroscopic sensor for acquiring information from the tissue according to an embodiment.
Figure 8:
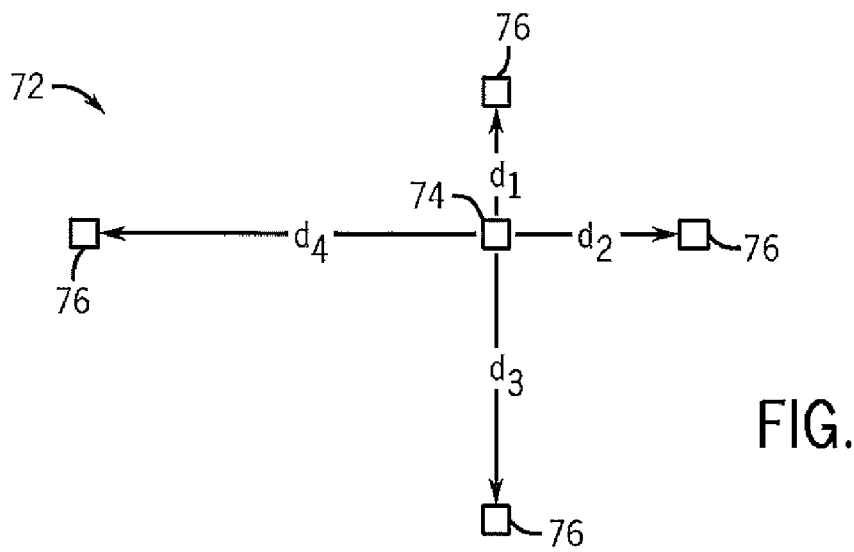
FIG. 8 is a top view of an example of a spectroscopic sensor with multiple detectors spaced apart from an emitter for acquiring information from the tissue according to an embodiment.

As noted, the sensor 72 may be incorporated into the ablation device 78 or, may, in other embodiments, be a separate device. FIGS. 7-8 show examples of configurations for the sensor 72. In FIG. 7, the emitter 74 is spaced apart from the detector 76 a particular distance that may be stored into the encoder 110, so that the monitor may perform the analysis of the mean photon penetration associated with a particular emitter-detector spacing. The emitter 74 may be capable of emitting light of multiple wavelengths. Depending on the wavelength, the mean photon penetration depth may be shallower, as shown for path 130, or may be deeper, as shown for path 132. By collecting data from different depths, a temperature gradient through the tissue may be determined.

In addition to using different wavelengths to acquire data at different depths, a sensor 72 may also incorporate additional detectors 76 with varied spacing around the emitter 74. As shown in FIG. 8, a sensor 72 may incorporate detectors spaced apart different distances (shown as distances $d_1$, $d_2$, $d_3$, and $d_4$) from an emitter 74. If the distances correspond with characteristic water absorption profiles and mean photon penetration depths, then any change that occurs during an ablation may be correlated to a empirically or mathematically-derived tissue temperature.

Figure 9:
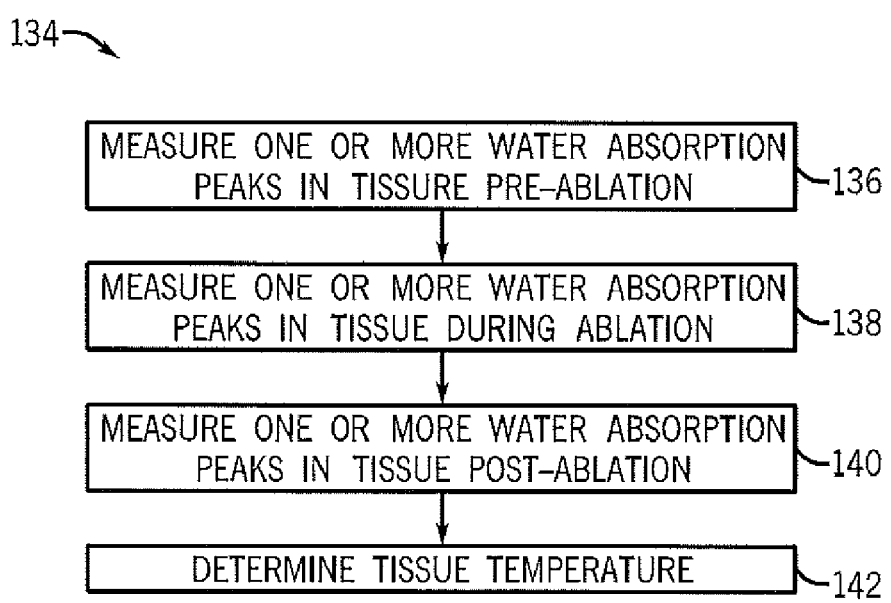
FIG. 9 is a block diagram of a method of monitoring tissue temperature during ablation.

FIG. 9 is a process flow diagram illustrating a method 134 for determining tissue temperature during an ablation procedure in accordance with some embodiments. The method may be performed as an automated procedure by a system, such as system 70. In addition, certain steps of the method may be performed by a processor, or a processor-based device such as a patient monitor 82 that includes instructions for implementing certain steps of the method 134. According to an embodiment, the method 134 begins with obtaining a baseline, pre-ablation signal representative of one or more water absorption peaks from detector 76 associated with the sensor 72 (block 136). The pre-ablation signal may be associated with normal body temperatures. The ablation device 78 may be activated and the sensor 72 may collect data during the ablation (block 138). The sensor 72 may also collect post-ablation data (block 140). The monitor 82 may perform analysis of the signals from the sensor 72 and calculation of the tissue temperature (block 142) based on the signal obtained.

For example, in one embodiment, the tissue temperature may be determined by examining changes in the water absorption peaks over the course of the ablation. If the change in the temperature is indicative of ablation (i.e., nonviability of the tissue), a monitor 82 may determine that a successful ablation has occurred. For example, tissue temperatures in excess of 43° C., 50° C., 60° C., or 80° C. may be indicative of ablation. In addition, such monitoring may include any appropriate visual indication, such as a display of a temperature or temperature versus depth, displayed on the monitor 82 or any appropriate audio indication. For example, an increase of tissue temperature above a predetermined viability threshold or outside of a predetermined range may trigger an alarm or may trigger an indication of ablation. Further, additional indications may include text or other alerts to inform that the ablation was likely successful.

While the invention may be susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A monitor, comprising:
   a sensor interface;
   a display; and
   data processing circuitry configured to:
   cause operation of a spectrophotometric sensor via the sensor interface, wherein the sensor comprises at least one emitter configured to emit light into a tissue of a patient and at least one detector configured to detect the light;
   receive spectrophotometric data associated with a mean photon penetration depth in the tissue from the at least one detector via the sensor interface;
   determine one or more temperatures of the tissue associated with the mean photon penetration depth from the spectrophotometric data; and
   cause the display to display an indication related to the one or more tissue temperatures.

2. The monitor of claim 1, wherein determining the one or more tissue temperatures comprises determining a change in a magnitude of a water absorption peak.

3. The monitor of claim 2, wherein determining the one or more tissue temperatures comprises correlating the change in the magnitude of the water absorption peak to a tissue temperature associated with the change in the magnitude of the water absorption peak.

4. The monitor of claim 1, wherein the data processing circuitry is configured to activate an energy source configured to direct ablating energy into the patient's tissue.

5. The monitor of claim 4, wherein the data processing circuitry comprises instructions for determining whether the tissue temperature is associated with heat from the ablating energy.

6. The monitor of claim 4, wherein the tissue temperature associated with heat from the ablating energy is greater than about 43° C.

7. The monitor of claim 1, wherein the determining the one or more tissue temperatures comprises determining a temperature gradient in the tissue from a plurality of mean photon penetration depths.

8. The monitor of claim 2, wherein determining the one or more tissue temperatures comprises determining a change in a shape of the water absorption peak.

9. The monitor of claim 1, wherein causing operation of a spectrophotometric sensor via the sensor interface comprises driving the emitter to emit light in a range from about 945 nm to about 1035 nm.

10. The monitor of claim 1, comprising receiving information related to a tissue ablation; and
    assessing the tissue ablation based on the tissue temperature.

11. The monitor of claim 10, wherein assessing the tissue ablation comprises determining a viability of the tissue.

12. The monitor of claim 10, wherein assessing the tissue ablation comprises determining a volume of ablated tissue.

13. The monitor of claim 5, wherein determining whether the tissue temperature is associated with heat from the ablating energy comprises comparing the tissue temperature to a baseline temperature.

14. The monitor of claim 13, wherein the baseline temperature comprises a local or systemic temperature of the patient.

15. The monitor of claim 13, wherein the baseline temperature comprises a temperature calculated based at least in part upon spectrophotometric data generated before ablating energy is directed into the patient's tissue.

16. The monitor of claim 1, wherein determining the one or more temperatures comprises using an estimation of lean water concentration in the tissue.

* * * * *